United States Patent
Kang et al.

(10) Patent No.: US 11,647,927 B2
(45) Date of Patent: May 16, 2023

(54) MICROELECTRODE ASSEMBLY FOR MONITORING OF IN VIVO NEUROTRANSMITTERS

(71) Applicant: SAMSUNG LIFE PUBLIC WELFARE FOUNDATION, Seoul (KR)

(72) Inventors: Min Hee Kang, Seoul (KR); Eun Kyoung Park, Seoul (KR); Soon Young Kwon, Seoul (KR); Kyu Sung Lee, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 445 days.

(21) Appl. No.: 16/758,138

(22) PCT Filed: Dec. 11, 2018

(86) PCT No.: PCT/KR2018/015650
§ 371 (c)(1),
(2) Date: Apr. 22, 2020

(87) PCT Pub. No.: WO2019/117575
PCT Pub. Date: Jun. 20, 2019

(65) Prior Publication Data
US 2020/0281488 A1 Sep. 10, 2020

(30) Foreign Application Priority Data

Dec. 13, 2017 (KR) ........................ 10-2017-0171128

(51) Int. Cl.
*A61B 5/24* (2021.01)
(52) U.S. Cl.
CPC .......... *A61B 5/24* (2021.01); *A61B 2562/028* (2013.01); *A61B 2562/0215* (2017.08)

(58) Field of Classification Search
CPC .............. A61B 5/24; A61B 2562/0215; A61B 2562/028; G01N 27/3272; G01N 27/3278
See application file for complete search history.

(56) References Cited

U.S. PATENT DOCUMENTS

| 9,833,145 B2 * | 12/2017 | Jeong ............... A61B 1/000095 |
| 2013/0137944 A1 * | 5/2013 | Jeong ................... A61B 5/0068 |
| | | 600/431 |

(Continued)

FOREIGN PATENT DOCUMENTS

| KR | 1020000000791 | 1/2000 |
| KR | 1020120015227 | 2/2012 |

(Continued)

OTHER PUBLICATIONS

Chen et al."Pt modified carbon fiber microelectrode for electrochemically catalytic reduction of hydrogen peroxide and its application in living cell H2O2 detection" J Electroanalytical Chemistry, 781:233-237 (2016).

(Continued)

*Primary Examiner* — Oyesola C Ojo
(74) *Attorney, Agent, or Firm* — Myers Bigel, P.A.

(57) ABSTRACT

A microelectrode assembly for in vivo neurotransmitter monitoring according to one embodiment of the present disclosure includes: a microelectrode part formed of a single strand; and a polymer coating layer surrounding the microelectrode part, wherein a portion of the microelectrode part may protrude from the polymer coating layer, neurotransmitters in vivo may be sensed by the protruding portion of the microelectrode part, and plasmonic nanostructures may be formed on the surface of the microelectrode part.

6 Claims, 7 Drawing Sheets

(56) References Cited

U.S. PATENT DOCUMENTS

2015/0250421 A1* 9/2015 Arumugam ........ A61B 5/14546
427/2.11
2019/0246923 A1* 8/2019 Yang ........................ A61B 5/24

FOREIGN PATENT DOCUMENTS

| KR | 1020150035345 | | 11/2013 | | |
|----|---|---|---|---|---|
| KR | 20140042711 A | * | 4/2014 | ......... | A61N 1/36135 |
| KR | 1020140042711 | | 4/2014 | | |
| KR | 20150035345 A | * | 4/2015 | ........... | A61N 1/4064 |

OTHER PUBLICATIONS

International Search Report corresponding to PCT/KR2018/015650, dated Mar. 21, 2019 (5 pages including English translation).

* cited by examiner

MICROELECTRODE ASSEMBLY FOR MONITORING OF IN VIVO NEUROTRANSMITTERS

CROSS REFERENCE TO RELATED APPLICATIONS

This application is a 35 U.S.C. § 371 national stage application of PCT International Application No. PCT/KR2018/015650, filed Dec. 11, 2018, which claims priority from Korean Patent Application No. 10-2017-0171128, filed Dec. 13, 2017, respectively, the contents of which are incorporated herein in their entireties by reference. The above-referenced PCT International Application was published in the Korean language as International Publication No. WO 2019/117575 A1 on Jun. 20, 2019.

TECHNICAL FIELD

The present disclosure relates to a microelectrode assembly for in vivo neurotransmitter monitoring, and more particularly, to a microelectrode assembly which includes a microelectrode having plasmonic nanostructures formed on the surface thereof and measures the electrochemical activity of neurotransmitters in real time using such plasmonic nanostructures.

BACKGROUND ART

In recent years, the need for technology for in vivo real-time monitoring of neurotransmitters has gradually increased. This is because the basal level of each type of neurotransmitter is an important factor in various brain diseases such as Parkinson's disease and schizophrenia, and hence there is a strong need for selective measurement of neurotransmitters and determination of basal levels of the neurotransmitters. Dopamine is a typical neurotransmitter secreted in the brain, and dopamine deficiency causes various brain neurological diseases. In particular, dopamine levels in patients with Parkinson's disease may be used as a feedback biomarker that can indicate the state of the disease.

According to the results of a previous study conducted using a microdialysis technique, the basal levels of neurotransmitters are about 5 nM to 20 nM for dopamine, about 200 to 300 pM for serotonin, and about 4 to 5 nM for adenosine. There is a need for the development of technology that can selectively measure the neurotransmitters present in such trace amounts. In an in vivo environment, various neurotransmitters are present in a mixed state, unlike those in a laboratory environment. Hence, the development of a technique for improving the selectivity to distinguish between the neurotransmitters to be measured is urgently needed for the advancement of treatment of brain diseases.

As methods for measuring neurotransmitters, various methods have been developed, such as a microdialysis technique and an enzyme-linked immunosorbent assay. However, these conventional methods have difficulty in measuring the real-time changes of neurotransmitters, due to their low temporal resolution (e.g., 1 minute or more), or are limited for the purpose of development of implantable medical devices or as methods for real-time measurement of neurotransmitter levels, due to the use of bulky devices.

Fast-Scan Cyclic Voltammetry (FSCV) can measure various neurotransmitters, such as dopamine, serotonin, norepinephrine, and adenosine, by a method of measuring current changes by causing a redox reaction. In addition, the FSCV has advantages in that it has a high temporal resolution at a scan rate of 10 times or more per second (10 Hz) and when a carbon microfiber electrode having a diameter of 30 μm (micrometers) or less is implanted into the brain, damage to brain tissue can be minimized. However, the FSCV has a disadvantage in that when a background subtraction method is used to determine the neurotransmitter levels, only changes in the levels can be determined and the basal levels cannot be determined. In addition, there is a problem in that it is very difficult to quantitatively measure the level of dopamine only by the FSCV, because ascorbic acid undergoes an oxidation process under physiological conditions similar to those for dopamine and the level of ascorbic acid is always higher than the level of dopamine.

Therefore, real-time monitoring of stimulation-induced changes in neurotransmitters requires technology capable of detecting neurotransmitters, which are present in trace amounts, with a high temporal resolution of 100 ms, a spatial resolution (e.g., detection sensitivity, specificity, etc.) of a few tens of μm (micrometers), and high sensitivity.

DISCLOSURE

Technical Problem

Electrochemical detection methods using conventional fast-scan cyclic voltammetry (FSCV) provide rapid and direct detection of neurotransmitters, but have a disadvantage in that the efficiency of detection is low due to very low levels of neurotransmitters in vivo as well as interference compounds in vivo. It can be expected that when a plasmonic nanostructure including an alloy of platinum having excellent catalytic activity and gold having excellent plasmonic properties is introduced to an FSCV microelectrode for cerebral implantation, the efficiency of detection of the electrochemical activities of neurotransmitters in vivo will be increased. Surface-enhanced Raman spectroscopy is a method capable of maximizing Raman signals using plasmonic metal nanoparticles and enables analysis at femtomolar levels. Simultaneous use of an FSCV microelectrode as a platform for surface-enhanced Raman spectroscopy can provide a method capable of directly detecting not only catecholamine-based neurotransmitters that are easily oxidized at present, but also various neurotransmitters.

Accordingly, one embodiment of the present disclosure intends to provide a microelectrode assembly for in vivo neurotransmitter monitoring.

Technical Solution

In accordance with one embodiment of the present disclosure, there may be provide a microelectrode assembly for in vivo neurotransmitter monitoring.

The microelectrode assembly for in vivo neurotransmitter monitoring according to one embodiment of the present disclosure includes: a microelectrode part formed of a single strand; and a polymer coating layer surrounding the microelectrode part, wherein a portion of the microelectrode part may protrude from the polymer coating layer, neurotransmitters in vivo may be sensed by the protruding portion of the microelectrode part, and plasmonic nanostructures may be formed on the surface of the microelectrode part.

The microelectrode part may be fabricated using carbon fiber so as to have predetermined diameter and protrusion length values.

Furthermore, the microelectrode part may be bonded to a silica tube, processed into a predetermined shape, by heat treatment of polyamic acid, and may be bonded to a wire using an electrically conductive material.

The polymer coating layer according to one embodiment of the present disclosure may be a membrane formed by surrounding and coating the microelectrode part excluding the protruding portion with polyimide so as to be insulated.

The plasmonic nanostructures may include an alloy including at least one selected from among gold, silver, platinum, palladium and aluminum, and may be formed by a predetermined method, wherein the predetermined method may be at least one selected from chemical synthesis, thermal deposition, electron beam evaporation, and sputtering deposition.

The microelectrode assembly according to one embodiment of the present disclosure may be bonded to a ferrule for optical fiber, and the ferrule may be used as a guide structure for depositing a metal thin layer on the microelectrode part.

Advantageous Effects

When the microelectrode assembly for in vivo neurotransmitter monitoring according to one embodiment of the present disclosure is simultaneously used as a platform for surface-enhanced Raman spectroscopy for FSCV, it is possible to rapidly and directly detect not only catecholamine-based neurotransmitters that are easily oxidized at present, but also various neurotransmitters.

In addition, the microelectrode assembly may be effectively used for the diagnosis, treatment and prognostic observation of declines in brain function, sensory function and motor function.

The microelectrode assembly may be clinically actively used for neuropathic pain, Parkinson's disease, epilepsy, quadriplegia, urinary incontinence, gastroparesis-related nausea, chronic ventilatory insufficiency, etc., thereby promoting the diagnosis and treatment of patients.

The microelectrode assembly enables the development of brain-related treatment techniques, which can improve the rehabilitation ability of patients and improve the quality of life of paralyzed patients and disabled persons.

BEST MODE

Figure 1:
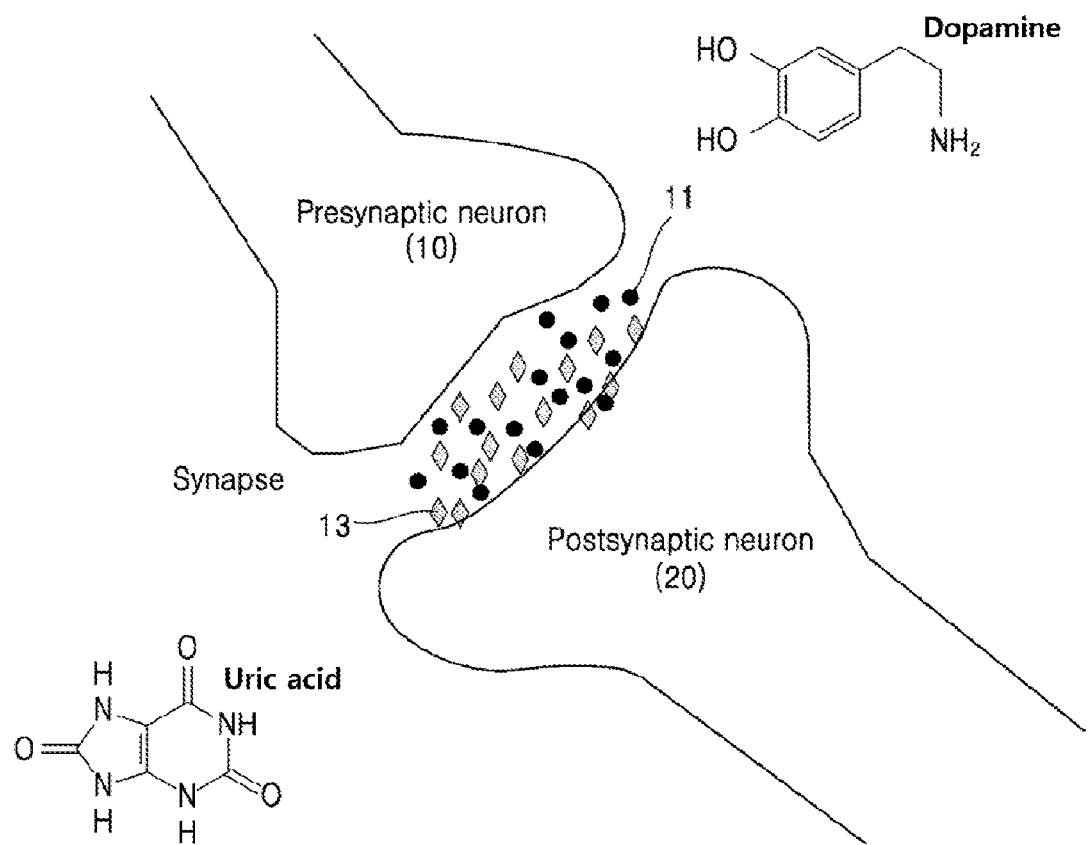
FIG. 1 is a schematic diagram showing the movement of neurotransmitters between neurons.

In accordance with one embodiment of the present disclosure, there may be provide a microelectrode assembly for in vivo neurotransmitter monitoring.

The microelectrode assembly for in vivo neurotransmitter monitoring according to one embodiment of the present disclosure includes: a microelectrode part formed of a single strand; and a polymer coating layer surrounding the microelectrode part, wherein a portion of the microelectrode part may protrude from the polymer coating layer, neurotransmitters in vivo may be sensed by the protruding portion of the microelectrode part, and plasmonic nanostructures may be formed on the surface of the microelectrode part.

The microelectrode part may be fabricated using carbon fiber so as to have predetermined diameter and protrusion length values.

Furthermore, the microelectrode part may be bonded to a silica tube, processed into a predetermined shape, by heat treatment of polyamic acid, and may be bonded to a wire using an electrically conductive material.

The polymer coating layer according to one embodiment of the present disclosure may be a membrane formed by surrounding and coating the microelectrode part excluding the protruding portion with polyimide so as to be insulated.

The plasmonic nanostructures may include an alloy including at least one selected from among gold, silver, platinum, palladium and aluminum, and may be formed by a predetermined method, wherein the predetermined method may be at least one selected from chemical synthesis, thermal deposition, electron beam evaporation, and sputtering deposition.

The microelectrode assembly according to one embodiment of the present disclosure may be bonded to a ferrule for optical fiber, and the ferrule may be used as a guide structure for depositing a metal thin layer on the microelectrode part.

MODE FOR INVENTION

Hereinafter, embodiments of the present disclosure will be described in detail so that they can be readily carried out by those skilled in the art to which the present disclosure pertains. However, the present disclosure may be embodied in various different forms and is not limited to the embodiments described herein. In the drawings, parts irrelevant to the description are omitted in order to clearly describe the present disclosure, and like reference numerals designate like parts throughout the specification.

Terms used in the present specification will be briefly described, and the present disclosure will be described in detail.

The terms used in the present disclosure may be currently widely used general terms selected in consideration of functions in the present disclosure, but may vary according to the intents of those skilled in the art, precedents, or the advent of new technology. In addition, in a particular case, terms arbitrarily selected by the applicant may be used, and in this case, their meanings will be described in detail in the relevant section of the description of the disclosure. Accordingly, the terms used in the present disclosure shall be defined based on the meanings thereof and the contents throughout the specification, rather than the simple names of the terms.

Throughout the specification, it is to be understood that when any part is referred to as "including" any component, it does not exclude other components, but may further include other components, unless otherwise specified. In addition, as used in the specification, the term " . . . part", "module", etc. refers to a unit for processing at least one function or operation, which may be implemented by hardware, software, or a combination of hardware and software. Furthermore, throughout the specification, when any part is referred to as being "connected" to another part, it refers to not only a case where any part is connected directly to another part, but also a case where any part is connected to another part "with a third element interposed therebetween".

Neurotransmitters refer to substances that modulate the signal transmission of the nervous system in vivo, such as dopamine, ascorbic acid, and uric acid. Such neurotransmitters are present in very small amounts in vivo. Thus, for accurate determination for the diagnosis of disease, treatment, prognostic observation, etc. of a patient, it should be able to accurately detect neurotransmitters in vivo in real time. The use of a microelectrode assembly for in vivo neurotransmitter monitoring according to one embodiment of the present disclosure can accurately detect neurotransmitters in vivo in real time compared to a conventional art.

Hereinafter, the present disclosure will be described in detail with reference to the accompanying drawings.

Figure 2:
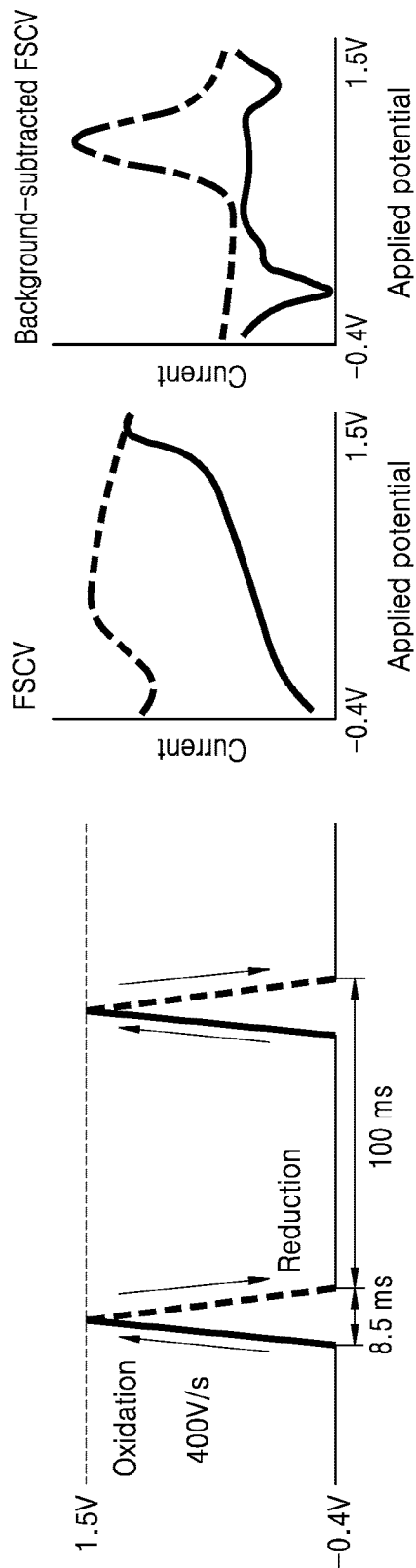
FIG. 2 shows waveform cyclic voltammograms obtained by conventional fast-scan cyclic voltammetry (FSCV).
Figure 3:
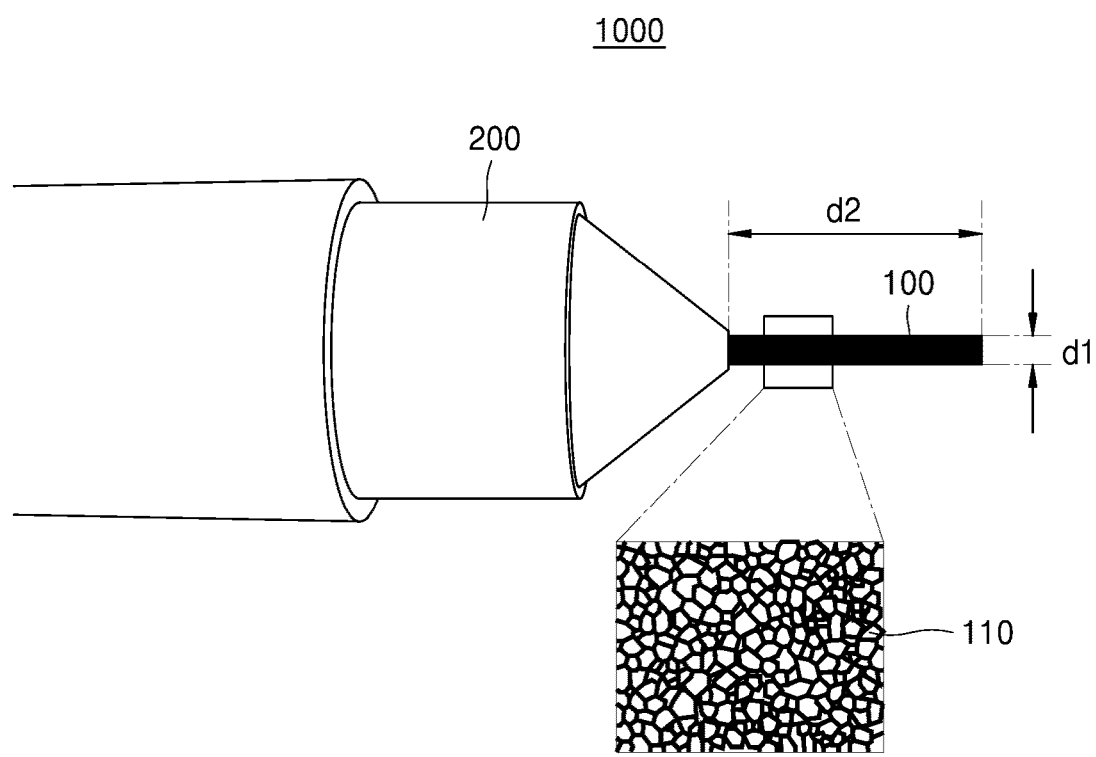
FIG. 3 is a conceptual diagram of a microelectrode assembly for in vivo neurotransmitter monitoring according to one embodiment of the present disclosure.
Figure 4:
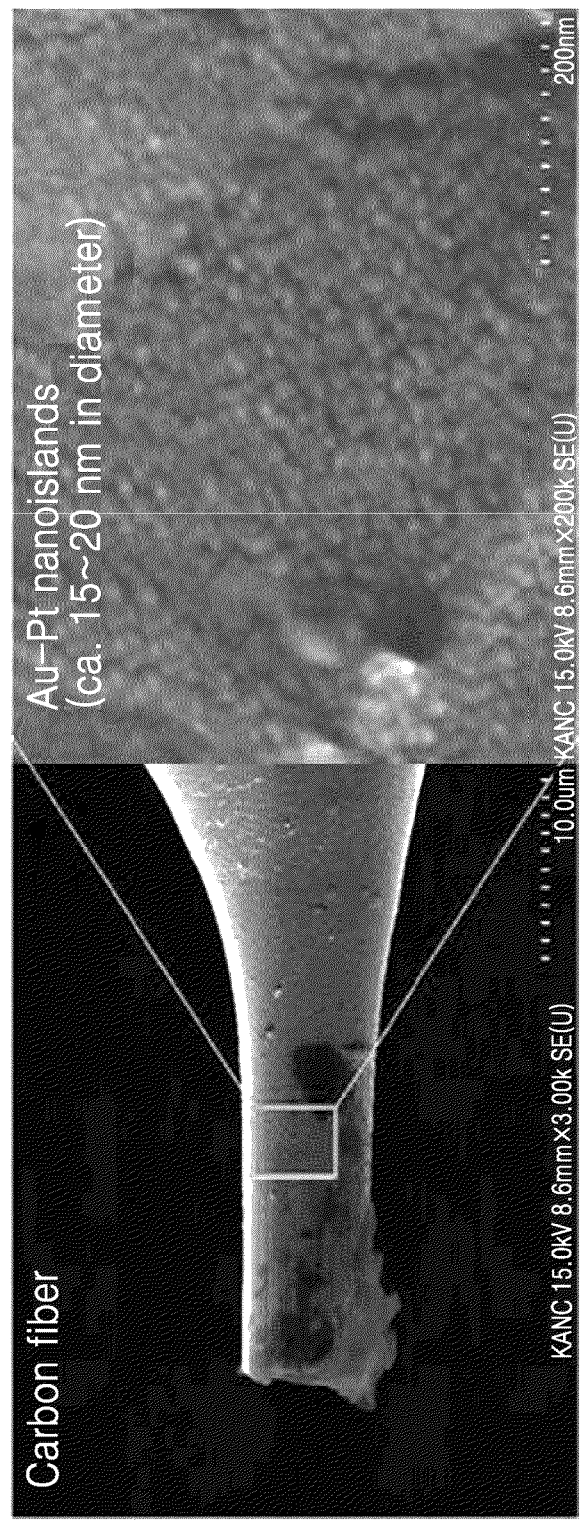
FIG. 4 shows plasmonic nanostructures of gold and platinum, formed on a microelectrode part according to one embodiment of the present disclosure.
Figure 5:
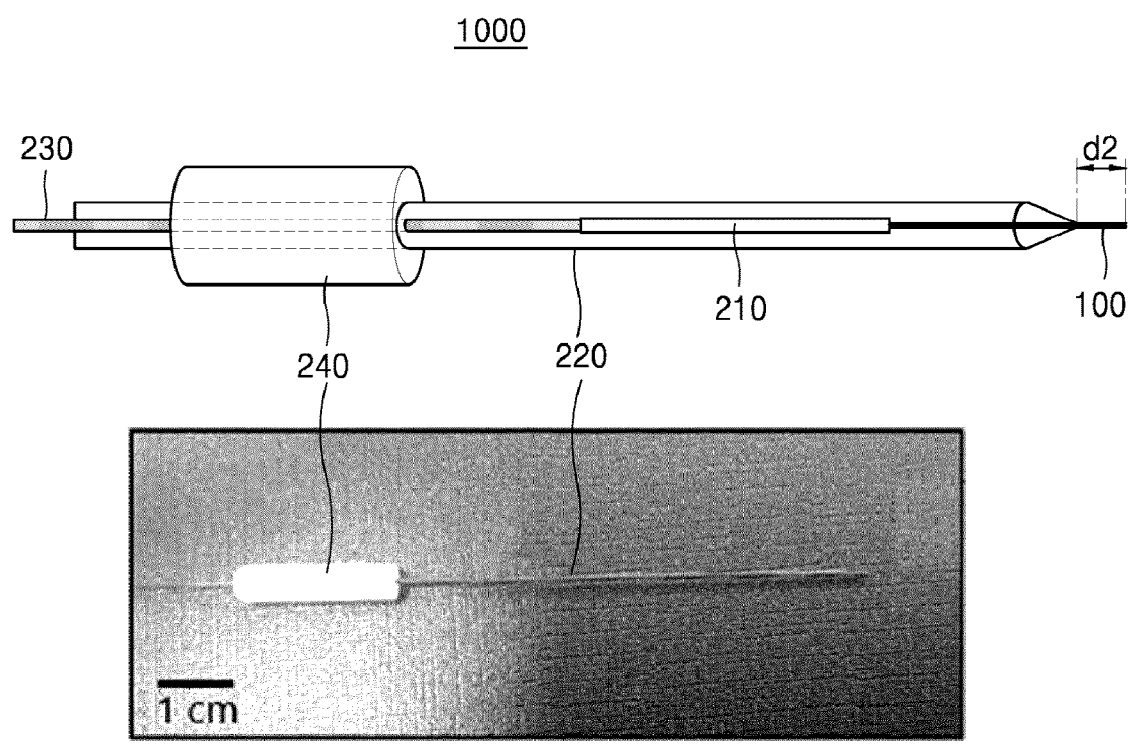
FIG. 5 shows a microelectrode assembly bonded to a ferrule according to one embodiment of the present disclosure.
Figure 6A:
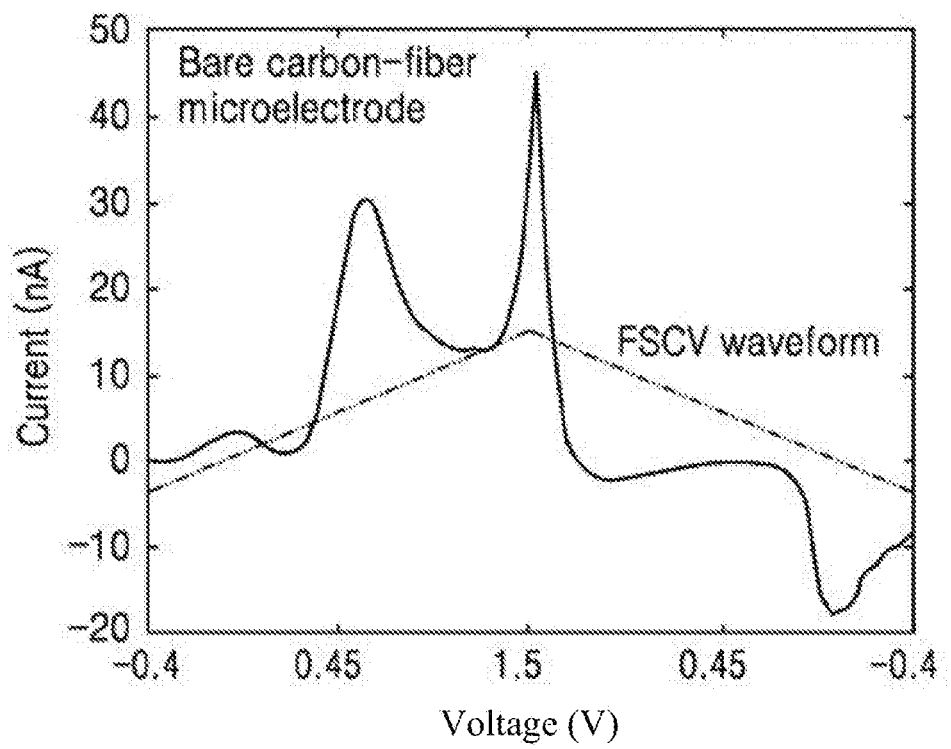
FIG. 6A shows the results of measuring dopamine signals using a conventional carbon fiber microelectrode.
Figure 6B:
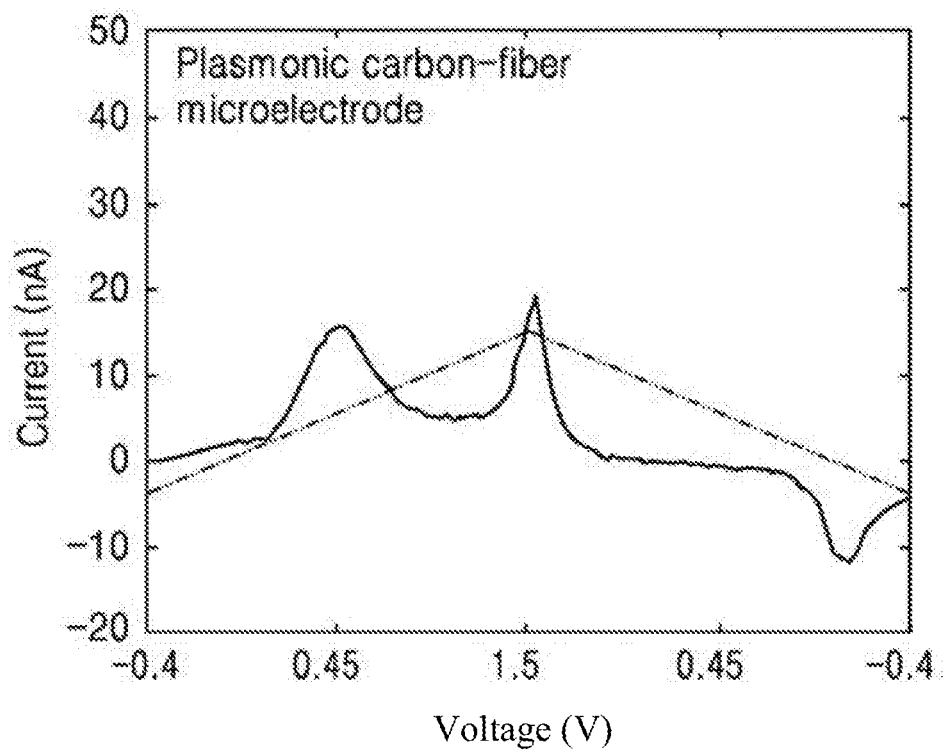
FIG. 6B shows the results of measuring dopamine signals using a plasmonic microelectrode assembly according to one embodiment of the present disclosure.
Figure 7:
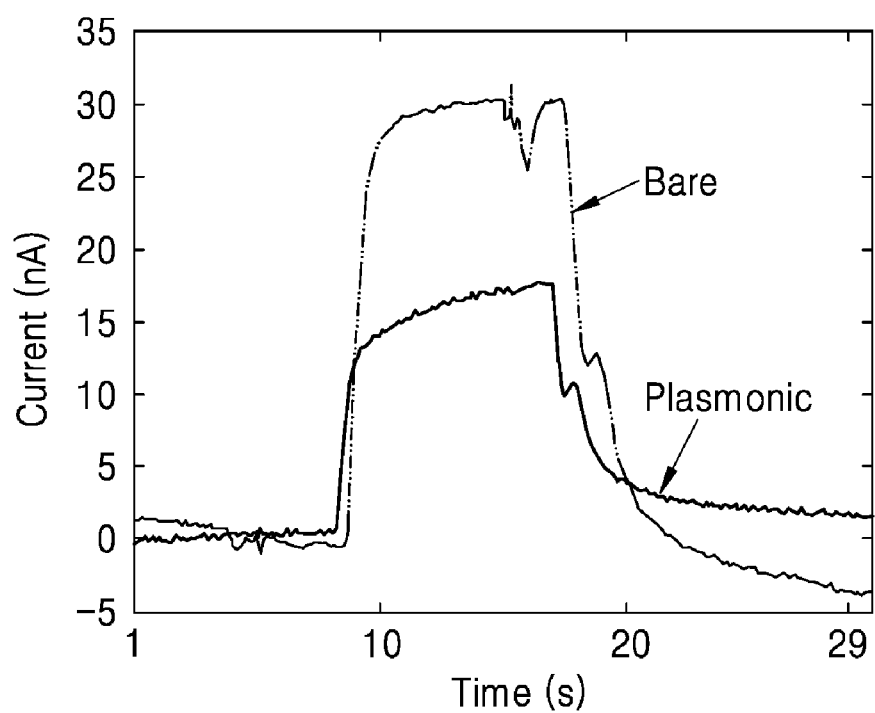
FIG. 7 shows a time response following dopamine injection.

FIG. 1 is a schematic diagram showing the movement of neurotransmitters between neurons, and FIG. 2 shows waveform cyclic voltammograms obtained by conventional fast-scan cyclic voltammetry (FSCV). FIG. 3 is a conceptual diagram of a microelectrode assembly for in vivo neurotransmitter monitoring according to one embodiment of the present disclosure, and FIG. 4 shows plasmonic nanostructures of gold and platinum, formed on a microelectrode part according to one embodiment of the present disclosure. FIG. 5 shows a microelectrode assembly bonded to a ferrule according to one embodiment of the present disclosure, and FIG. 6A shows the results of measuring dopamine signals using a conventional carbon fiber microelectrode, and FIG. 6B shows the results of measuring dopamine signals using a plasmonic microelectrode assembly according to one embodiment of the present disclosure. FIG. 7 shows a time response following dopamine injection.

Dopamine (DA), ascorbic acid (AC) and uric acid (UA) are neurotransmitters that play a very important role in metabolic pathways in vivo. Dopamine is a neurotransmitter that modulates the signaling of the nervous system in vivo and acts as a major therapeutic agent against drug addiction and Parkinson's disease, and uric acid is the final product of the purine metabolic pathway, and abnormal levels of uric acid are very closely associated with many neuropsychiatric disorders. Rapid and accurate detection of such neurotransmitters present in very small amounts in vivo is very important for the purpose of early diagnosis or treatment of various brain neurological diseases.

Referring to FIG. 1, such neurotransmitters may move and be transferred from a presynaptic neuron 10 to a postsynaptic neuron 20. In other words, a first neurotransmitter 11, a second neurotransmitter 13 and the like may move between the neurons, thereby performing the signaling of the nervous system or modulating the signaling. For example, the first neurotransmitter 11 may be dopamine, and the second neurotransmitter 13 may be uric acid.

For rapid and precise detection of such neurotransmitters present in trace amounts, fast scan cyclic voltammetry (FSCV) using carbon fiber microelectrodes has been utilized. The carbon fiber microelectrodes have been used for the detection of neurotransmitters, because they are small in size and easy to fabricate and have good electrical properties and biological compatibility, especially for catecholamine-based compounds. In addition, the carbon fiber microelectrode is small in size, and thus has an advantage in that when the microelectrode is used, brain damage in the implantation/removal procedures for the patient's brain can be minimized. As shown in FIG. 2, conventional electrochemical detection methods using the FSCV provide rapid and direct detection of neurotransmitters, but have a problem in that the efficiency of detection is low due to very low levels of neurotransmitters in vivo as well as interference compounds in vivo. In other words, there is a strong need for a method of increasing the detection efficiency of neurotransmitters by increasing electrochemical signals, temporal resolution, spatial resolution, etc.

Fast-Scan Cyclic Voltammetry (FSCV) is a method of measuring current changes by causing a redox reaction and can measure various neurotransmitters, such as dopamine, serotonin, norepinephrine, and adenosine. In addition, the FSCV has advantages in that it has a high temporal resolution at a scan rate of 10 times or more per second (10 Hz) and when a carbon microfiber electrode having a diameter of 30 μm (micrometers) or less is implanted into the brain, damage to brain tissue can be minimized. However, the FSCV has a disadvantage in that when a background subtraction method is used to determine the neurotransmitter levels, only changes in the levels can be determined and the basal levels cannot be determined. In addition, there is a problem in that it is very difficult to quantitatively measure the level of dopamine only by the FSCV, because ascorbic acid undergoes an oxidation process under physiological conditions similar to those for dopamine and the level of ascorbic acid is always higher than the level of dopamine.

Raman spectroscopy technology may be used as a method having fast time resolution and increased detection efficiency. The energy absorbed or emitted by materials after light incidence is closely related to the molecular structure of each material and vibrational energy, and the spectrum of light due to Raman scattering is unique to each material. Raman spectroscopy has been used for the qualitative and quantitative analysis of materials, but in recent years, there have been attempts to apply Raman spectroscopy to studies on analysis of the intracellular or extracellular biochemical and morphological information of biological tissues. However, when tissue is irradiated with a laser in the visible range, a fluorescence or luminescence phenomenon occurs in addition to Rayleigh scattering or Raman scattering, and in this case, the fluorescence or luminescence has intensity, which is very stronger than the Raman scattering, and occurs in a region similar to a region in which a Raman spectrum is measured. Hence, the fluorescence or luminescence is also measured during measurement of the Raman spectrum, making it impossible to obtain a pure Raman spectrum. The Raman spectral signal is very weak, and thus difficult to apply to real-time monitoring of a material present in a very small amount. The Raman spectral signal can be increased by a method of increasing the output of a laser which is incident excitation light, but the use of a high-power laser is limited because it induces the deformation of biomolecules.

Surface-enhanced Raman spectroscopy using the microelectrode assembly according to one embodiment of the present disclosure is a method capable of maximizing Raman signals using plasmonic metal nanoparticles and enables analysis at femtomolar levels. When the microelectrode for FSCV according to one embodiment of the present disclosure is simultaneously used as a platform for surface-enhanced Raman spectroscopy, it can provide a method capable of directly detecting not only catecholamine-based neurotransmitters that are easily oxidized at present, but also various neurotransmitters.

Plasmonic metal (e.g., gold, silver, platinum, etc.) nanostructures using localized surface plasmon resonance (LSPR) phenomena may be applied in various fields, including the fields of optoelectronic devices, biosensors, optics, catalysts, etc. Platinum-based catalysts have a high activity for oxygen reduction, and when the platinum catalysts become nanostructured, they may have greater electrocatalytic activity. Therefore, when plasmonic nanostructures including an alloy of platinum (Pt) having excellent catalytic activity and gold (Au) having excellent plasmonic properties are introduced to, for example, a microelectrode for cerebral implantation, as in the microelectrode assembly according to one embodiment of the present disclosure, it is possible to increase the detection efficiency of the electrochemical activities of neurotransmitters in vivo, making it possible to detect very small amounts of neurotransmitters without markers in real time. The electrochemical and optical properties of the microelectrode assembly may be controlled by controlling the kind of metal nanomaterial, the size of the plasmonic nanostructures, the composition ratio, and the like. If the FSCV is performed using the microelectrode assembly according to one embodiment of the present disclosure, the spatial and temporal resolutions of electrochemical signals may be significantly increased compared to those in a conventional art.

Referring to FIGS. 3 and 5, a microelectrode electrode 1000 for in vivo neurotransmitter monitoring according to one embodiment of the present disclosure may include: a microelectrode part 100 formed of a single strand; and a polymer coating layer 200 surrounding the microelectrode part 100, wherein a portion of the microelectrode part 100 may protrude from the polymer coating layer 200, neurotransmitters in vivo may be sensed by the protruding portion of the microelectrode part 100, and plasmonic nanostructures 110 may be formed on the surface of the microelectrode part 100.

The microelectrode part 100 may be fabricated using carbon fiber so as to have a predetermined diameter d1 and a protruding length value d2. In addition, the microelectrode part 100 may also be a doped diamond electrode. The predetermined diameter d1 and the protruding length value d2 may be predetermined differently according to the subject to be tested, the site to be tested, and the type of testing. For example, the predetermined diameter d1 may be 7 μm (micrometers), and the protruding length value d2 may be 100 μm (micrometers).

Furthermore, the microelectrode part 100 may be bonded to a silica tube 210, processed into a predetermined shape, by heat treatment of polyamic acid, and may be bonded to a wire 230 using an electrically conductive material. The wire 230 according to one embodiment of the present disclosure may refer to a signal transmission wire made of nitinol which is a nickel-titanium alloy. Nitinol is a non-magnetic alloy obtained by mixing nickel and titanium at about 1:1, and this alloy material has the property of returning to its original shape when it is heated above a certain temperature or immersed in water, even after it undergoes deformation such as distortion after produced as a product. Even after a product made of nitinol is deformed, it bounces back to its original state when it is immersed in water. Thus, these rotational forces are used, and nitinol is also referred to as a shape memory alloy.

As shown in FIGS. 3 and 5, the polymer coating layer 200 according to one embodiment of the present disclosure may be a membrane formed by surrounding and coating the microelectrode part 100 excluding the protruding portion with polyimide so as to be insulated.

The plasmonic nanostructures 110 may include at least one selected from among gold, silver, platinum, palladium and aluminum, and may be formed by a predetermined method. In addition, these plasmonic nanostructures 110 may be formed of an alloy of the above-described metals, and the predetermined method may be at least one method selected from chemical synthesis, thermal deposition, electron beam evaporation, and sputtering deposition.

According to one embodiment of the present disclosure, a first metal thin layer and a second metal thin layer, which have a thickness on the order of nanometers, may be deposited on carbon fiber by at least one method selected from among thermal deposition, electron beam evaporation, and sputtering deposition. In other words, according to one embodiment of the present disclosure, the alloyed plasmonic nanostructures may be formed using at least one selected from thermal deposition, electron beam evaporation, and sputtering deposition, in addition to a conventional chemical synthesis method. The pattern of the first metal thin layer may be different from the pattern of the second metal thin layer. Furthermore, the first metal thin layer and the second metal thin layer may also be deposited on carbon fiber so as to have a laminated structure by crossing them in the same pattern. Each of the metal thin layers may be formed using at least one of gold, silver, platinum, palladium and aluminum, and the composition ratio of the metals may be determined according to the controlled thickness of each metal thin layer.

The microelectrode assembly 1000 according to one embodiment of the present disclosure may be bonded to a ferrule 240 for optical fiber, and the ferrule 240 may be used as a guide structure for depositing the metal thin layer on the microelectrode part 100.

As shown in FIG. 5, the microelectrode part 100 may be made of, for example, single carbon fiber having a diameter d1 of 7 μm (micrometers). This microelectrode part 100 may be bonded to a silica tube, having an inner diameter of 20 μm (micrometers) and an outer diameter of 90 μm (micrometers) and coated with polyimide to a thickness of 10 μm (micrometers), by heat treatment of polyamic acid.

In addition, the microelectrode part may be connected to the nitinol wire 230 using an electrically conductive silver paste.

A portion (e.g., 30 μm to 100 μm) of the microelectrode part and the nitinol wire 230, except for portions for sensing neurotransmitters, may be surrounded by a polyimide tube 220 so as to be insulated. Polyimide used as the insulating layer is a biocompatible material that has excellent mechanical strength and thermal and chemical stabilities, is flexible, and causes no tissue damage even when it is implanted in the human body for a long time. The properties of polyimide are as follows:

| Tensile Strength | 21.5 MPa | Glass Transition Temperature | 285° C. |
| Young's Modulus | 2.5 GPa | Coefficient of Thermal Expansion | 55 ppm/° C. |
| Tensile Elongation | 85% | Dielectric Constant Moisture Absorption | 3.2~3.3 1.08% |

The microelectrode assembly 1000 as described above may be combined and aligned with a ferrule (e.g., outer diameter: ø2.5 mm; bore size: ø270 μm±10 μm) for optical fiber, and then bonded to the ferrule using a bonding material (e.g., polydimethylsiloxane (PDMS)). This ferrule 240 may be used as a guide structure for depositing the metal thin layer on the microelectrode part 100. In addition, a jig, made of SUS and manufactured by precise machining, may be additionally used to fix the microelectrode bonded to the ferrule 240 in order to deposit the metal thin layer.

Using the microelectrode assembly 1000 for in vivo neurotransmitter monitoring according to one embodiment of the present disclosure, dopamine was monitored in real time. For an in vitro experiment, dopamine (Sigma Aldrich) was dissolved in 1 mM of Tris buffer (15 mM tris(hydroxymethyl) aminomethane, 3.25 mM KCl, 140 mM NaCl, 1.2 mM $CaCl_2$, 1.25 mM $NaH_2PO_4$, 1.2 mM $MgCl_2$, and 2.0 mM $Na_2SO_4$ (pH 7.4)) solution, and 0.1 M perchloric acid was added thereto in order to prevent the dopamine from being oxidized. Dopamine secretion was allowed to be able to mimic the secretion and resorption of neurotransmitters in vivo using a flow-cell, and the experiment was performed using an FSCV measurement system. Ag/AgCl was used as a reference electrode.

As shown in FIG. 6, a triangular waveform was used as an FSCV waveform for dopamine measurement, and setting was made so that the triangular waveform would be repeated every 100 ms at a scan rate of 400 V/s. While a voltage of −0.4<+1.5<−0.4 was applied at a frequency of 10 Hz, the current generated by the voltage application was measured, and 1 μM dopamine was injected using a flow-cell. After the dopamine injection, the current values caused by dopamine oxidation were measured. The current values caused by dopamine oxidation were an average of 30.5 nA for the conventional simple carbon-fiber microelectrode (a Bare carbon-fiber microelectrode in FIG. 6), and 15.7 nA for the microelectrode introduced with plasmonic structures according to one embodiment of the present disclosure (a Plasmonic carbon-fiber microelectrode in FIG. 6), indicating that the sensitivity to dopamine was somewhat changed. However, as shown in FIG. 7, from the time response to dopamine oxidation following dopamine injection, it was confirmed that the plasmonic microelectrode according to one embodiment of the present disclosure (Plasmonic in FIG. 7) responded more immediately than the conventional simple carbon-fiber microelectrode (Bare in FIG. 7). It is considered that, due to the Au—Pt alloy structures formed on the microelectrode part 100, the initial adsorption of dopamine decreased compared to that in the carbon-fiber microelectrode, and thus the sensitivity decreased. This absorption of dopamine can be changed by controlling the spacing between the Au—Pt nanostructures to increase the area of the adhesive surface. The increased time response is due to the catalytic activity of the Au—Pt nanostructures, and the sensitivity can also be simultaneously increased compared to that in the conventional art by optimizing the nanostructures as described above.

The numerical values described above are exemplary for description, and are not necessarily limited thereto. Furthermore, the above description of the present disclosure is exemplary, and those of ordinary skill in the art to which the present disclosure pertains will appreciate that the present disclosure can be easily modified into other specific forms without departing from the technical spirit or essential characteristics of the present disclosure. Therefore, it should be understood that the exemplary embodiments described above are exemplary in all aspects and are not restrictive. For example, each component described to be of a single type can be implemented in a distributed manner. Likewise, components described to be distributed can be implemented in a combined manner.

The scope of the present disclosure is defined by the following claims rather than by the detailed description of the disclosure. It should be construed that all modifications and embodiments conceived from the meaning and scope of the claims and their equivalents are included in the scope of the present disclosure.

What is claimed is:

1. A microelectrode assembly for in vivo neurotransmitter monitoring, the microelectrode assembly comprising:
a microelectrode part comprising a single strand; and
a polymer coating layer surrounding the microelectrode part,
wherein the microelectrode part comprises a protruding portion that protrudes from the polymer coating layer,
the protruding portion of the microelectrode part is configured to sense neurotransmitters in vivo,
plasmonic nanostructures are on a surface of the microelectrode part, and
wherein the plasmonic nanostructures comprise an alloy comprising one or more of gold, silver, platinum, palladium, and aluminum.

2. The microelectrode assembly of claim 1, wherein the microelectrode part is fabricated using carbon fiber so as to have predetermined diameter and protrusion length values.

3. The microelectrode assembly of claim 1, wherein the microelectrode part is bonded to a silica tube, processed into a predetermined shape, by heat treatment of polyamic acid, and is configured to be bonded to a wire using an electrically conductive material.

4. The microelectrode assembly of claim 1, wherein the polymer coating layer is a membrane formed by surrounding and coating the microelectrode part excluding the protruding portion with polyimide so as to be insulated.

5. The microelectrode assembly of claim 1, wherein the plasmonic nanostructures are formed by a predetermined method, and wherein the predetermined method comprises one or more of chemical synthesis, thermal deposition, electron beam evaporation, and sputtering deposition.

6. The microelectrode assembly of claim 1, wherein the microelectrode assembly is configured to be bonded to a ferrule for optical fiber, and the ferrule is configured to be used as a guide structure for depositing a metal thin layer on the microelectrode part.

* * * * *